United States Patent [19]
Lajeunesse

[11] Patent Number: 5,592,687
[45] Date of Patent: Jan. 14, 1997

[54] FACIAL INSULATOR

[76] Inventor: Alan L. Lajeunesse, 11 Ellerton St., Chicopee, Mass. 01020

[21] Appl. No.: 535,647

[22] Filed: Sep. 28, 1995

[51] Int. Cl.⁶ ..................................................... A41D 13/00
[52] U.S. Cl. ........................................ 2/9; 2/206; 2/455
[58] Field of Search ................................... 2/9, 206, 2, 7, 2/8, 243.1, 267; 602/54, 57, 43, 58, 61, 74; 128/857, 858, 888

[56] References Cited

U.S. PATENT DOCUMENTS

| | | | |
|---|---|---|---|
| 1,436,313 | 11/1922 | Hafer | 2/206 |
| 2,667,869 | 2/1954 | D'Elia | 2/9 |
| 3,594,813 | 7/1971 | Sanderson | 2/2 |
| 4,040,127 | 8/1977 | Slovitt et al. | 2/9 |
| 4,534,342 | 8/1985 | Paxa | 602/74 |
| 4,635,625 | 1/1987 | Teeple | 602/74 |
| 4,674,133 | 6/1987 | Oschner | 2/206 |
| 4,773,408 | 9/1988 | Cilento et al. | 128/156 |
| 4,984,302 | 1/1991 | Lincoln | 2/206 |
| 5,153,040 | 10/1992 | Faasse, Jr. | 602/57 |
| 5,244,457 | 9/1993 | Karami et al. | 602/55 |
| 5,274,847 | 1/1994 | Lauttamus | 2/9 |
| 5,308,313 | 5/1994 | Karami et al. | 602/55 |
| 5,395,675 | 3/1995 | Altholz et al. | 602/54 |
| 5,476,443 | 12/1995 | Cartmell et al. | 602/57 |

Primary Examiner—Amy B. Vanatta
Attorney, Agent, or Firm—Malcolm J. Chisholm, Jr.

[57] ABSTRACT

An improved facial insulator is disclosed for restricting heat loss from exposed skin surfaces. In a general embodiment, the facial insulator comprises a support pad having a design surface for displaying a design and an opposed adhesive surface having an edge strip along a perimeter edge of the pad and an insulating area defined by the edge strip as a circumference of the insulating area. A pressure-sensitive adhesive covers the edge strip, and an insulating material is affixed to the insulating area of the adhesive surface of the insulating pad. At least one downstream vent break and at least one upstream vent break are in generally opposed locations on the edge strip for permitting air to flow through the insulating material to remove any perspiration or moisture. A release layer is affixed to and covers the adhesive surface of the support pad. In a further embodiment, the facial insulator of the present invention may comprise a facial insulator set including insulators dimensioned in the shape of thin-flesh facial areas such as a nose bridge facial insulator and a pair of upper cheek bone facial insulators, so that only those thin-flesh areas are covered; and the vent breaks of the nose bridge and upper cheek bone facial insulators are positioned along their edge strips to facilitate movement of ordinary air currents through the insulating material, such as air currents passing over exposed facial skin surfaces of a down hill skier.

14 Claims, 3 Drawing Sheets

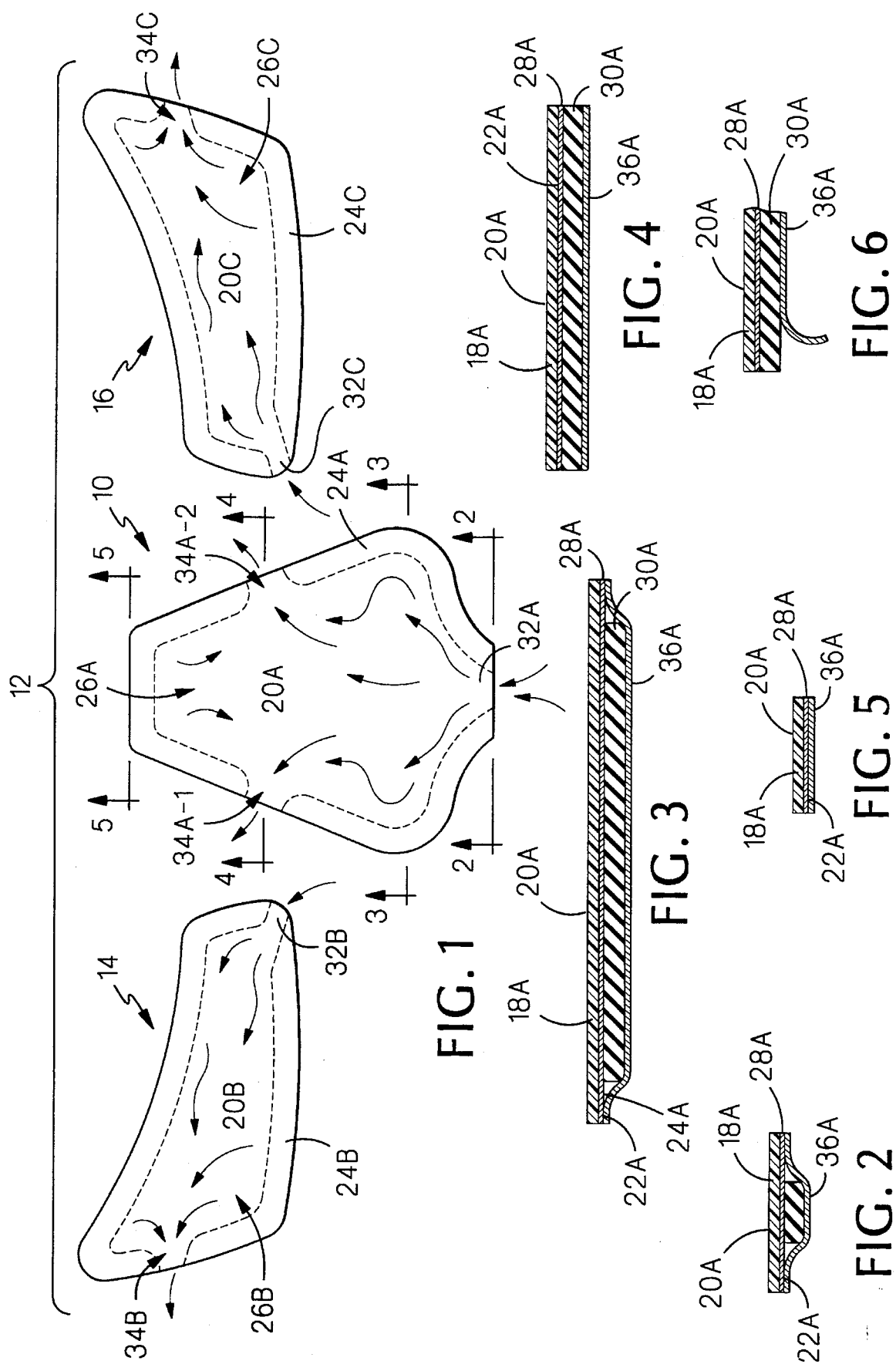

5,592,687

FACIAL INSULATOR

BACKGROUND OF THE INVENTION

The present invention relates to insulating devices for restricting heat loss, and in particular relates to insulating devices for use by a participant in cold weather recreational activities, such as down hill skiing.

Down hill skiers experience significant heat loss from exposed skin surfaces resulting from both the cold weather inherent to their sport as well as from rapid air flow across the exposed skin surfaces during skiing. Typically exposed skin surfaces are limited to facial areas of down hill skiers, and most of those areas are covered by head wear, such as caps or hoods, and eye shields, such as goggles. Because of the bright sun light reflected off of the snow, etc., it is very common that skiers' goggles are tinted, and cover from the mid-forehead to just below the skiers' eyes, excluding the nose. Raised collar jackets, or sweaters, etc. often cover up to the chin area, while upper foreheads and ears are covered by the caps or hoods. That leaves primarily the skier's nose, mouth and cheek areas exposed to rapid heat loss.

When the heat loss is so high that protection of skiers' nose, mouth and cheek areas is necessary, the protection has typically included either a face mask, or a scarf to cover those areas, both of which are quite awkward, bulky and unattractive, thereby detracting from the skiers' mobility, comfort and personal appearance. Additionally, known face masks cover an area between the nose and cheeks so that exhausted breath leaving a skier's nose or mouth is directed by the ordinary airflow over the skier's face into contact with the exterior and/or the interior surface of the goggles, resulting in condensation of the moisture in the breath on the goggles in the form of a film of fog, or even ice upon freezing of the moisture. Consequently, known methods of inhibiting heat loss from the nose, mouth and cheek areas of a down hill skier have proven to be ineffective, unattractive, and even disruptive of the skier's performance through physical limitations to head movement and/or to vision through the skiers' goggles.

Accordingly, it is the general object of the present invention to provide an improved facial insulator that overcomes the problems of the prior art.

It is a more specific object to provide an improved facial insulator that facilitates insulation of exposed facial skin surfaces without hindering mobility, attractiveness or vision of a user of the insulator.

It is yet another specific object to provide an improved facial insulator that does not impede flow of exhausted breath of a user so that the vision of the user through eye goggles is not impeded by use of the insulator.

It is still another object to provide an improved facial insulator that enhances the attractiveness of the user through application of variable appealing designs to the insulator.

It is another object of to provide an improved facial insulator that may be worn outdoors and indoors without accumulation of excess heat.

It is an additional object to provide an improved facial insulator that may be manufactured, distributed and purchased at a very low cost.

These and other objects and advantages of this invention will become more readily apparent when the following description is read in conjunction with the accompanying drawings.

SUMMARY OF THE INVENTION

An improved facial insulator is disclosed for restricting heat loss from exposed skin surfaces. In a general embodiment, the facial insulator comprises a support pad having a design surface for displaying a design and an adhesive surface opposed to the design surface of the pad, the adhesive surface having an edge strip defined along a perimeter edge of the pad and an insulating area defined by the edge strip as a circumference of the insulating area; a pressure-sensitive adhesive covering the edge strip; an insulating material affixed to the insulating area of the adhesive surface of the insulating pad; at least one downstream vent break and at least one upstream vent break in generally opposed positions on the edge strip for permitting air to flow across the edge strip, so that a current of air may move into the downstream vent break, through the insulating material, and out of the upstream vent break to remove any accumulated moisture within the insulating material; and a release layer affixed to and covering the adhesive surface of the support pad that may be peeled away to expose the pressure sensitive adhesive along the edge strip surrounding the insulating material, so that a user may secure the facial insulator to an exposed facial skin surface.

In a preferred embodiment, the facial insulator of the present invention may comprise a facial insulator set including insulators dimensioned in the shape of thin-flesh facial areas such as a nose bridge facial insulator and a pair of upper cheek bone facial insulators, so that only those thin-flesh areas are covered; and the vent breaks of the nose bridge and upper cheek bone facial insulators are positioned along their edge strips to facilitate movement of ordinary air currents through the insulating material, such as air currents passing over exposed facial skin surfaces of a down hill skier. In a further preferred embodiment, generally opposed box-like projections of the insulating material extend across the edge strips to define the vent breaks. In use of the facial insulators, a down hill skier would remove the release layers from the adhesive surfaces of the support pads and secure the pressure sensitive adhesive along the edge strips to the exposed skin surfaces to be protected so that the design surfaces are exposed to the air. The design surfaces may bear the trademark or logo of the skier's preferred ski equipment, or may bear a fanciful design suggestive of the skier's persona. The vent breaks are positioned so that onrushing air currents would enter through the downstream vent break and exit through the upstream vent break.

BRIEF DESCRIPTION OF THE DRAWINGS

FIG. 1 is a flat plan view of facial insulators constructed in accordance with the present invention showing a facial insulator set including a nose bridge facial insulator and a pair of upper cheek bone facial insulators having phantom lines designating edge strips of the insulators and having arrows designating flow patterns of currents of air passing through vent breaks in the edge strips of the facial insulators.

FIG. 2 is a cross-sectional view of the FIG. 1 nose bridge facial insulator taken along view line 2—2.

FIG. 3 is a cross-sectional view of the FIG. 1 nose bridge facial insulator taken along view line 3—3.

FIG. 4 is a cross-sectional view of the FIG. 1 nose bridge facial insulator taken along view line 4—4.

FIG. 5 is a cross-sectional view of the FIG. 1 nose bridge facial insulator taken along view line 5—5.

FIG. 6 is a cross-sectional view of the FIG. 1 nose bridge facial insulator showing a release layer being released from insulating material of the facial insulator.

DESCRIPTION OF THE PREFERRED EMBODIMENTS

Figure 7:
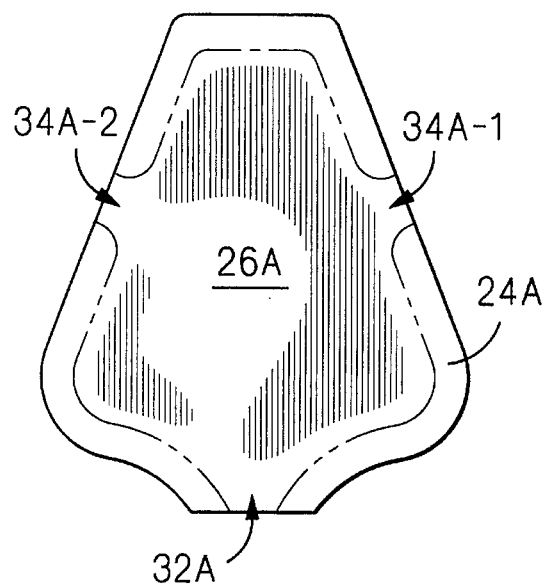
FIG. 7 is flat plan view of an adhesive surface of the FIG. 1 nose bridge facial insulator.
Figure 8:
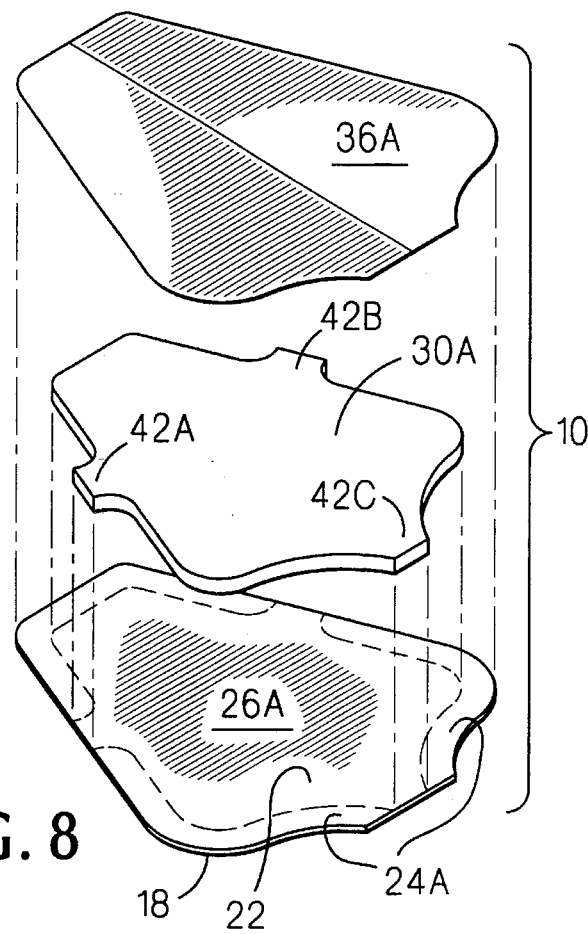
FIG. 8 is an exploded perspective view of the FIG. 1 nose bridge facial insulator showing a release layer and insulating material suspended over the adhesive surface of the facial insulator.
Figure 9:
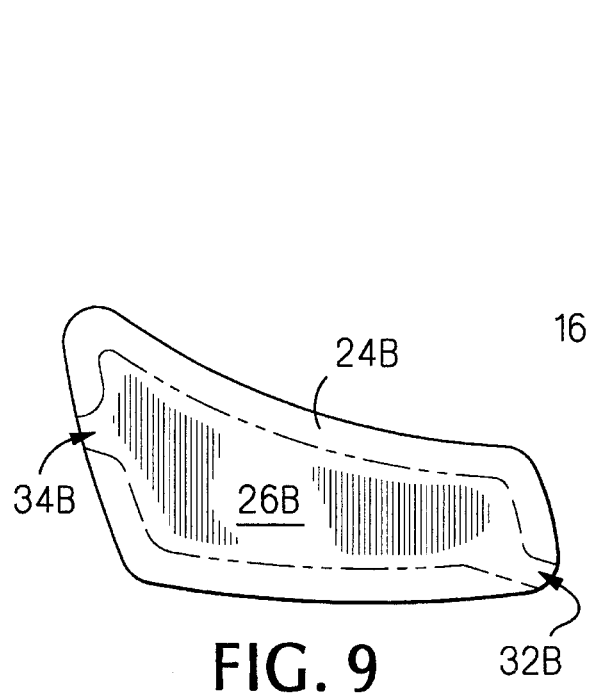
FIG. 9 is a flat plan view of an adhesive surface of one of the FIG. 1 upper cheek bone facial insulators.

Referring to the drawings in detail, improved facial insulators of the present invention are shown in FIGS. 1–11 and a general or single-piece embodiment is best shown in FIG. 8 and is designated by the reference numeral 10. As best seen in FIGS. 1, the single piece embodiment of the facial insulator 10 may be included in a facial insulator set 12 wherein the single-piece embodiment 10 serves as a nose bridge facial insulator and the facial insulator set also includes a left upper cheek bone facial insulator 14 and a right upper cheek bone facial insulator 16 which left and right upper cheek bone facial insulators are generally mirror images of each other. The facial insulators 10, 14, 16 have common components that will be designated by specific reference numerals in this description and on the accompanying drawings followed by the letter "A" for the single-piece or nose bridge facial insulator 10; followed by the letter "B" for the left upper cheek bone facial insulator; and, followed by the letter "C" for the right upper cheek bone facial insulator.

As shown in FIGS. 2–6, each facial insulator 10, 14, and 16 includes a support pad 18A, 18B, 18C having an outer or design surface 20A, 20B, 20C for displaying a design; an inner or adhesive surface 22A, 22B, 22C opposed to the design surface 20A, 20B, 20C of the pad 18A, 18B, 18C, the adhesive surface 22A, 22B, 22C having an edge strip 24A, 24B, 24C defined along a perimeter of the pad 18A, 18B, 18C, the adhesive surface also having an insulating area 26A, 26B, 26C (best seen in FIGS. 7–10) defined by the edge strips 24A, 24B, 24C as a circumference of the insulating area; a layer of pressure sensitive adhesive 28A, 28B, 28C covering at least the edge strip 24A, 24B, 24C; an insulating material 30A, 30B, 30C affixed to the insulating area 26A, 26B, 26C; at least one downstream vent break 32A, 32B, 32C, and at least one upstream vent break 34A-1, 34A-2, 34B, 34C (the single-piece facial insulator described in FIGS. 1–5, 7 and 8 having two upstream vent breaks designated respectively "34A-1 and 34A-2"); and a release layer 36A, 36B, 36C affixed to and covering the adhesive surface 22A, 22B, 22C, of the support pad 18.

Figure 11:
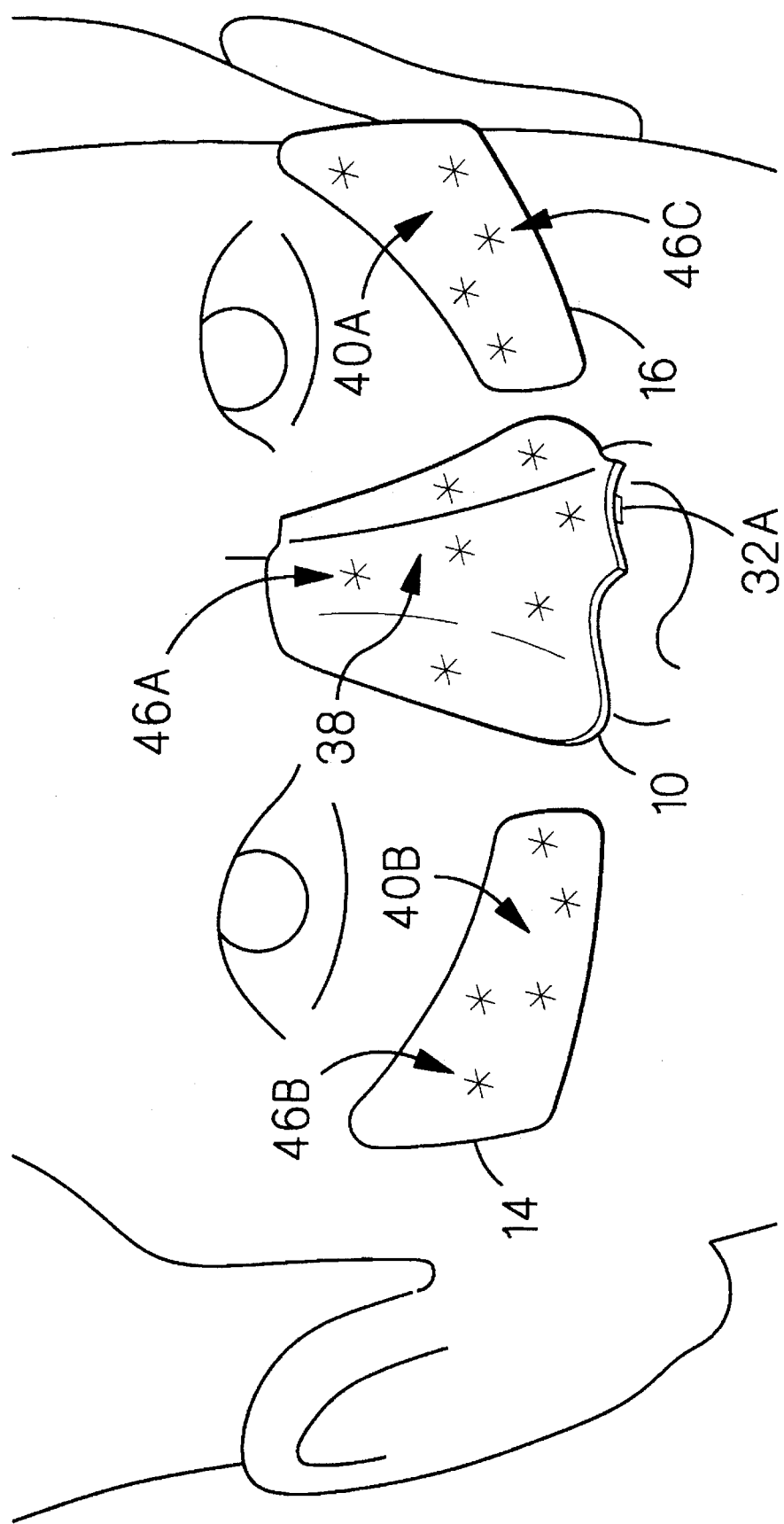
FIG. 11 is perspective view showing application of the FIG. 1 facial insulator set to a user.

It is known that within nose, mouth and cheek areas of typical down hill skiers, only those skin surfaces having proportionately lower blood flow within a close proximity of the skin surface suffer risk of discomfort and/or injury resulting from severe heat loss during down hill skiing. In other words, those areas having the greatest depth of flesh, and therefore blood flow, are able to quickly replace heat lost, while those areas with least depth of flesh, and therefore less blood flow, are at risk of injury due to heat loss. In particular, the bridge of the down hill skiers' nose has but a thin layer of flesh between the skin and the cartilage making up the nose compared to the depth of flesh in the central cheeks or around the mouth. Similarly, those portions of skin adjacent the left and right portions of the maxilla and zygoma below and parallel to a bottom border of each eye socket (herein referred to as "the upper cheek bone areas") also have only a thin layer of flesh between the bone and the skin. It has been found that those area are especially susceptible to discomfort and/or injury resulting from heat loss during down hill skiing. Consequently the facial insulator set 12 shown in FIGS. 1 and 11 includes components dimensioned to cover and insulate those areas. In particular, the single-piece or nose bridge facial insulator 10 of FIGS. 1 and 11 is dimensioned to cover and therefore insulate a user's nose bridge 38 (shown in FIG. 11), while the left and right upper cheek bone facial insulators 14, 16 are dimensioned to cover and therefore insulate a user's upper cheekbone areas 40B, 40C (shown in FIG. 11).

The support pad 18A, 18B, 18C of the improved facial insulators 10, 12, 14 of the present invention may be manufactured of any common material well-known in the art that is commonly used for dressing minor skin wounds, such as the well known "BAND-AID" bandage or wound dressing. The layer of pressure sensitive adhesive 28A, 28B, 28C may comprise any of a variety of adhesives well known in the art for application to human skin, such as a copolymer of isooctyl acrylate and acrylic acid as described at Column 4 of U.S. Pat. No. 4,773,408 to Cilento et al., which Patent is hereby incorporated by reference. The insulating material 30A, 30B, 30C may comprise any of a variety of insulators well known in the art, such as a gauze of cotton of other natural or synthetic materials. The release layer 36A, 36B, 36C may comprise any of a variety of release papers well known in the art, such as a silicone coated paper, that does not bond to the pressure sensitive adhesive and may be easily pealed away from the pressure sensitive adhesive layer 28A, 28B, 28C.

Figure 10:
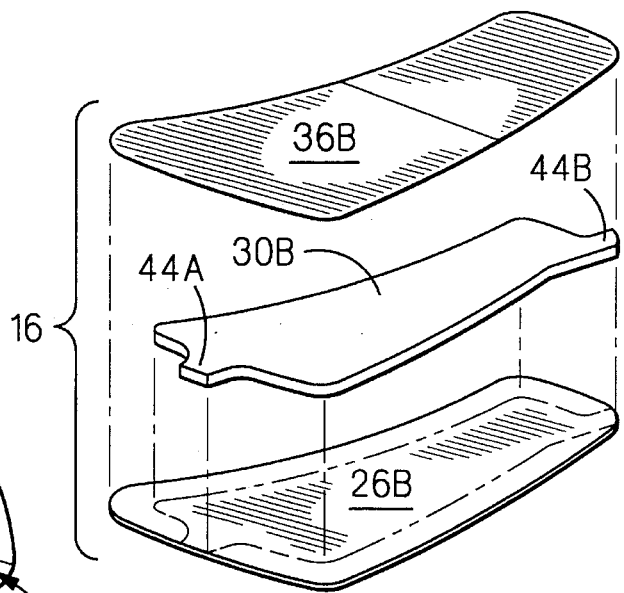
FIG. 10 is an exploded perspective view of one of the FIG. 1 upper cheek bone facial insulators showing a release layer and insulating material suspended over the adhesive surface of the facial insulator.

In manufacture of the improved facial insulators 10, the pressure sensitive adhesive layer may be applied only to the edge strips 24A, 24B, 24C, or to the entire adhesive surface 22A, 22B, 22C. Next, the insulating material 30A, 30B, 30C is secured to the adhesive surface, and the release layer 36A, 36B, 36C is next applied over the insulating material and edge strip 24A, 24B, 24C. The downstream vent break 32A, 32B, 32C and upstream vent break 34A-1, 34A-2, 34B, 34C may comprise a vent break means for permitting a current of air to enter the downstream vent break, pass through the insulating material 30A, 30B, 30C, and exit the upstream vent break, such as by box-like projections of the insulating material 30A, 30B, 30C over the adjacent edge strip 24A, 24B, 24c. As best shown in FIGS. 8 and 10, the box like projections for the nose bridge facial insulator 10 are give reference numerals 42A, 42B, 42C for insulating material 30A, and are given reference numerals 44A, 44B for insulating material 30B. The vent break means may also comprise any structure or arrangement that permits a current of air to pass through the downstream vent break, insulating material and out the upstream vent break (as represented by the air-current flow arrows in FIG. 1), such as portions of the edge strip 24A, 24B, 24C having no pressure sensitive adhesive layer, the portions being positioned on at least two generally opposed positions along the edge strip.

It has been found with down hill skiers in particular that the skiers experience alternating periods of high energy output while they are skiing and periods of low energy output while they are waiting to get on chair lifts, and generally ascending the mountain, etc. During the periods of high energy output a skier's face is likely to exude much more perspiration or moisture than during the periods of low energy output. Consequently, the passage of air currents through the downstream vent breaks, insulating material and upstream vent breaks of the present improved facial insulators 10 during the periods of high energy output beneficially causes the accumulated perspiration from the skier's face to be removed as air currents pass over and around the skier's face as a result of the ordinary movement of down hill skiing. Removal of the perspiration prevents accumulated moisture from forming a thermal bridge within the facial insulator that would otherwise hasten transfer of heat out of the user's skin and across an insulator adjacent the skin. During periods of low energy output, however, movement of air currents through an insulator must be minimized to resist movement of heat across the insulator. Because the downstream vent breaks 32A, 32B, 32C, and upstream vent breaks 34A-1, 34A-2, 34B, 34C, of the present invention are at the periphery of the support pad 18A, 18B, 18C, movement of air currents through the improved facial insulators of the present invention is minimized during periods of low energy output because currents of air passing by a down hill skier are at a minimum during those periods of low energy output. In a particular embodiment of the improved facial insulators 10, the support pad 18A, 18B, 18C is non-porous, unlike ordinary material used to dress minor skin wounds such as common bandages, so that movement of air through the insulating material during periods of low energy output of a user is kept to an absolute minimum to further resist heat loss from the user's skin.

In use of the improved facial insulators 10 of the present invention and of a facial insulator set 12 in particular, a user (not shown) would select a set 12 that bore on its design surface 20A, 20b, 20C a desired design, trademark or logo, such as the snow flake design 46A, 46B, 46C shown on FIG. 11. The user would then simply peel off the release layer 36A, 36B, 36C and then press the pressure sensitive adhesive layer 28A, 28B, 28C on the edge strips 24A, 24B, 24C, onto appropriate nose bridge 38 and upper cheekbone 40A, 40B positions, as shown in FIG. 11, so that the insulating material contacts the nose bridge and upper cheek bone areas. As the down hill skier moved down a ski slope, ordinary air currents passing next to the skier's face would enter the facial insulators 10, 12, 14 through the downstream vent breaks 32A, 32B, 32C, and then pass through the insulating material 30A, 30B, 30C to remove out of the upstream vent breaks 34A, 34B, 34C any moisture accumulated as a result of the skier's increased perspiration during a high energy period of down hill skiing. After the skier reaches the bottom of the ski slope and during a lower energy or lower perspiration period, while the skier is waiting to get on a lift, or is on a lift ascending the slope, less air moves through the insulating material 30A, 30B, 30C, thereby enhancing it resistance to heat loss from the adjacent skin.

While the present improved facial insulator invention has been described and illustrated with respect to a particular application to a downhill skier, it will be understood by those skilled in the art that the present invention is not limited to this particular example. For example, the facial insulators could be modified slightly to apply to an ice fishing environment wherein users are typically exposed to periods of high and low wind, or the facial insulators could be applied to a motorcycle environment to limit heat loss without the bulk of a full shield. Accordingly, reference should be made primarily to the attached claims rather than the foregoing specification to determine the scope of the invention.

I claim:

1. An improved facial insulator for restricting heat loss from exposed skin surfaces, comprising:
   a. a support pad having a design surface for displaying a design, and having an opposed adhesive surface, the adhesive surface having an edge strip defined along a perimeter edge of the pad and an insulating area defined by the edge strip as a circumference of the insulating area;
   b. a pressure sensitive adhesive layer covering the edge strip;
   c. an insulating material affixed to the insulating area;
   d. at least two vent break means positioned at generally opposed locations on the edge strip for permitting a current of air to pass over the edge strip; and,
   e. a release layer affixed to and covering the edge strip and insulating material so that upon removal of the release layer from the edge strip and insulating material the pressure sensitive adhesive layer secures the support pad to the exposed skin surface and one vent break means permits the current of air to move into the insulating material and the at least one other vent break means permits the current of air to move through and out of the insulating material.

2. The improved facial insulator of claim 1, wherein the vent break means comprises a box-like projection of the insulating material over a portion of the edge strip and over the pressure sensitive adhesive layer adjacent that portion of the edge strip.

3. The improved facial insulator of claim 1, wherein the vent break means comprises a portion of the edge strip having no pressure sensitive adhesive layer.

4. The improved facial insulator of claim 1, wherein the support pad is non-porous.

5. An improved facial insulator set for restricting heat loss from exposed skin surfaces, comprising a nose bridge facial insulator, a left upper cheek bone facial insulator, and a right upper cheek bone facial insulator for restricting heat loss from a user's nose bridge and left and right upper cheekbones, wherein the nose bridge, left upper cheek bone and right upper cheek bone facial insulators each comprise:
   a. a support pad having a design surface for displaying a design, and having an opposed adhesive surface, the adhesive surface having an edge strip defined along a perimeter edge of the pad and an insulating area defined by the edge strip as a circumference of the insulating area;
   b. a pressure sensitive adhesive layer covering the edge strip;
   c. an insulating material affixed to the insulating area;
   d. at least two vent break means positioned at generally opposed locations on the edge strip for permitting a current of air to pass over the edge strip; and,
   e. a release layer affixed to and covering the edge strip and insulating material so that upon removal of the release layer from the edge strip and insulating material the pressure sensitive adhesive layer secures the support pad to the exposed skin surface and one vent break means permits the current of air to move into the insulating material and the at least one other vent break means permits the current of air to move through and out of the insulating material.

6. The improved facial insulator set of claim 5, wherein each vent break means comprises a box-like projection of the insulating material over a portion of the edge strip and over the pressure sensitive adhesive layer adjacent that portion of the edge strip.

7. The improved facial insulator set of claim 5, wherein each vent break means comprises a portion of the edge strip having no pressure sensitive adhesive layer.

8. The improved facial insulator set of claim 5, wherein each support pad is non-porous.

9. An improved facial insulator set for restricting heat loss from exposed skin surfaces, comprising a nose bridge facial insulator, a left upper cheek bone facial insulator, and a right upper cheek bone facial insulator for restricting heat loss from a user's nose bridge and left and right upper cheekbones, wherein the nose bridge, left upper cheek bone and right upper cheek bone facial insulators each comprise:

a. a support pad having a design surface for displaying a design, and having an opposed adhesive surface, the adhesive surface having an edge strip defined along a perimeter edge of the pad and an insulating area defined by the edge strip as a circumference of the insulating area;

b. a pressure sensitive adhesive layer covering at least portions of the edge strip; and, c. an insulating material affixed to the insulating area so that the pressure sensitive adhesive layer secures the insulating material adjacent the exposed skin.

10. The improved facial insulator set of claim 9, wherein each facial insulator includes at least two vent breaks positioned at generally opposed locations on the edge strip for permitting a current of air to pass over the edge strips and through the insulating material.

11. The improved facial insulator set of claim 10, wherein each vent break comprises a box-like projection of the insulating material over a portion of the edge strip and over the pressure sensitive adhesive layer adjacent that portion of the edge strip.

12. The improved facial insulator set of claim 10, wherein each vent break comprises a portion of the edge strip having no pressure sensitive adhesive layer.

13. The improved facial insulator set of claim 10, wherein each support pad is non-porous.

14. The improved facial insulator set of claim 10, wherein each facial insulator further includes a release layer affixed to and covering the edge strip and insulating material so that upon removal of the release layer from the edge strip and insulating material the pressure sensitive adhesive layer secures the support pad to the exposed skin surface.

\* \* \* \* \*